(12) United States Patent
Karehed et al.

(10) Patent No.: US 8,637,471 B2
(45) Date of Patent: Jan. 28, 2014

(54) FERTILIZATION PREDICTION AND PROMOTION

(75) Inventors: Karin Karehed, Uppsala (SE); Helena Akerud, Uppsala (SE)

(73) Assignee: Karolinska Institutet Innovations AB, Solna (SE)

( * ) Notice: Subject to any disclaimer, the term of this patent is extended or adjusted under 35 U.S.C. 154(b) by 0 days.

(21) Appl. No.: 13/638,878

(22) PCT Filed: Mar. 31, 2011

(86) PCT No.: PCT/SE2011/050365
§ 371 (c)(1),
(2), (4) Date: Oct. 1, 2012

(87) PCT Pub. No.: WO2011/123041
PCT Pub. Date: Oct. 6, 2011

(65) Prior Publication Data
US 2013/0053330 A1 Feb. 28, 2013

Related U.S. Application Data

(60) Provisional application No. 61/320,034, filed on Apr. 1, 2010.

(51) Int. Cl.
*C07K 7/08* (2006.01)
*A61B 17/435* (2006.01)
*G01N 21/75* (2006.01)
*A61K 38/10* (2006.01)
*A61P 15/08* (2006.01)
*C07K 14/435* (2006.01)
*A61K 38/17* (2006.01)

(52) U.S. Cl.
USPC ......... 514/21.3; 530/324; 530/327; 514/21.5; 435/6.11; 436/501; 600/34

(58) Field of Classification Search
None
See application file for complete search history.

(56) References Cited

U.S. PATENT DOCUMENTS 6,649,344 B1 11/2003 Lindenberg et al.
2001/0041670 A1 11/2001 Simantov et al.

FOREIGN PATENT DOCUMENTS

| JP | 2007/282553 A | | 11/2007 |
| WO | WO 02/064621 | * | 8/2002 |
| WO | WO 02/064621 A2 | | 8/2002 |
| WO | WO 02/076486 A2 | | 10/2002 |
| WO | WO 2005/003162 A2 | | 1/2005 |

OTHER PUBLICATIONS

Hennis B.C. et al., "An amino acid polymorphism in histidine-rich glycoprotein (HRG) explains 59% of the variance in plasma HRG levels", *Thrombosis and Haemostasis*, Dec. 1995; 74(6): 1497-1500.
Hennis B.C. et al., "Identification and genetic analysis of a common molecular variant of histidine-rich glycoprotein with a difference of 2kD in apparent molecular weight", *Thrombosis and Haemostasis*, Dec. 1995; 74(6): 1491-1496.
Kårehed et al., "Fibrinogen and histidine-rich glycoprotein in early-onset preeclampsia", *Acta Obstetricia et Gynecologica*, 2010; 89: 131-139.

* cited by examiner

*Primary Examiner* — Cecilia J Tsang
*Assistant Examiner* — Tara Martinez
(74) *Attorney, Agent, or Firm* — Myers Bigel Sibley & Sajovec, PA (57) ABSTRACT

The outcome of an in vitro fertilization (IVF) of a woman in terms of chances of successful pregnancy or the fertility status of a woman is predicted based on nucleotide analysis of the histidine-rich glycoprotein (HRG) gene or protein analysis of HRG. The proline isoform of HRG or an amino acid fragment thereof can further be used to increases the success of pregnancy of a woman.

8 Claims, 5 Drawing Sheets

```
                        SEQUENCE LISTING

<160> NUMBER OF SEQ ID NOS: 9

<210> SEQ ID NO 1
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 1 gtg cgg aac tgc ycc aga cac cat ttc                                27
Val Arg Asn Cys Xaa Arg His His Phe
1               5

<210> SEQ ID NO 2
<211> LENGTH: 9
<212> TYPE: PRT
<213> ORGANISM: Homo sapiens
<220> FEATURE:
<221> NAME/KEY: misc_feature
<222> LOCATION: (5)..(5)
<223> OTHER INFORMATION: The 'Xaa' at location 5 stands for Pro, or Ser.

<400> SEQUENCE: 2

Val Arg Asn Cys Xaa Arg His His Phe
1               5

<210> SEQ ID NO 3
<211> LENGTH: 27
<212> TYPE: DNA
<213> ORGANISM: Homo sapiens

<400> SEQUENCE: 3
gcagggcggg tcacaaggtc catagtc                                      27

<210> SEQ ID NO 4
<211> LENGTH: 20
<212> TYPE: DNA
<213> ORGANISM: Homo sapiens
```

<400> SEQUENCE: 4
cacaagttct gtctcttcag                                                    20

<210> SEQ ID NO 5
<211> LENGTH: 19
<212> TYPE: DNA
<213> ORGANISM: Homo sapiens

<400> SEQUENCE: 5
gaaggtggtc ggagtcaac                                                     19

<210> SEQ ID NO 6
<211> LENGTH: 22
<212> TYPE: DNA
<213> ORGANISM: Homo sapiens

<400> SEQUENCE: 6
cagagttaaa agcagccctg gt                                                 22

<210> SEQ ID NO 7
<211> LENGTH: 35
<212> TYPE: PRT
<213> ORGANISM: Homo sapiens
<300> PUBLICATION INFORMATION:
<308> DATABASE ACCESSION NUMBER: GenBank/BAA21613
<309> DATABASE ENTRY DATE: 2008-09-19
<313> RELEVANT RESIDUES IN SEQ ID NO: (187)..(221)

<400> SEQUENCE: 7

Arg Gly Gly Glu Gly Thr Gly Tyr Phe Val Asp Phe Ser Val Arg Asn
1               5                   10                  15

Cys Pro Arg His His Phe Pro Arg His Pro Asn Val Phe Gly Phe Cys
            20                  25                  30

Arg Ala Asp
        35

<210> SEQ ID NO 8
<211> LENGTH: 35
<212> TYPE: PRT
<213> ORGANISM: Homo sapiens

<400> SEQUENCE: 8

Arg Gly Gly Glu Gly Thr Gly Tyr Phe Val Asp Phe Ser Val Arg Asn
1               5                   10                  15

Cys Ser Arg His His Phe Pro Arg His Pro Asn Val Phe Gly Phe Cys
            20                  25                  30

Arg Ala Asp
        35

<210> SEQ ID NO 9
<211> LENGTH: 14
<212> TYPE: PRT
<213> ORGANISM: Homo sapiens
<300> PUBLICATION INFORMATION:
<308> DATABASE ACCESSION NUMBER: GenBank/BAA21613
<309> DATABASE ENTRY DATE: 2008-09-19
<313> RELEVANT RESIDUES IN SEQ ID NO: (198)..(211)

<400> SEQUENCE: 9

Phe Ser Val Arg Asn Cys Pro Arg His His Phe Pro Arg His
1               5                   10

FERTILIZATION PREDICTION AND PROMOTION

STATEMENT OF PRIORITY

This application is a 35 U.S.C. §371 national phase application of International Application Serial No. PCT/SE2011/050365, filed Mar. 30, 2011, which claims the benefit, under 35 U.S.C. §119 (e), of U.S. Provisional Application Ser. No. 61/320,034, filed Apr. 1, 2010, the entire contents of which are incorporated by reference herein it their entireties.

TECHNICAL FIELD

The present invention generally relates to fertilization, and in particular to techniques for predicting the chances of success of fertilization and for increasing the chances of successful fertilization.

BACKGROUND

More than 12% of the reproductive population worldwide has had difficulties in conceiving and a majority of the women affected of infertility are between the ages of 15 and 44. Infertility is the most common medical disorder among women in these ages. The couples might be helped by an assisted reproductive technique, such as in vitro fertilization (IVF).

IVF is a process by which egg cells are fertilized by sperm in vitro outside the womb. IVF is a major treatment in infertility when other methods of assisted reproductive technology have failed. The process typically involves hormonally controlling the ovulatory process, removing ova from the woman's ovaries and letting sperm fertilize them in a fluid or culture medium to form zygotes that are matured into embryos. A formed embryo is then transferred to the patient's uterus with the intent to establish a successful pregnancy.

Although the pregnancy rate, i.e. the success rate for pregnancy following IVF, has increased a lot the last few years clinical studies report an average pregnancy rate of up to 70% in industrial countries, possible after several trials. A lot of research has been invested in the field of trying to increase this pregnancy rate even further. The research has up until now suggested several different hormone substances that are thought to increase the pregnancy rate, for instance by improving embryo implantation rates and decreasing miscarriage rates.

Another technique has been presented in U.S. Pat. No. 6,649,344. The patent document discloses an assay for a predictive marker to indicate the presence of non-fertilizable ova capable of in vitro maturation (IVM) and subsequent IVF in a mammal. The assay is based on determining the presence and relative concentration of Inhibin A or Estradiol in a blood sample at various times during the menstrual cycle.

There is still a need for a technique that allows identification of those patients that have good or poor chances for successful pregnancy and in particular for couples undergoing IVF and a technique to improve the chances of successful pregnancy.

SUMMARY

It is an objective to provide a technique of enabling identification of subjects having good respective poor chances of successful pregnancy.

It is another objective to provide a technique that can be used to increase the chances of successful pregnancy of a woman.

These and other objectives are met by embodiments as disclosed herein.

Briefly, an aspect relates to a method of predicting outcome of an IVF. The method comprises determining the isoform(s) of Histidine-rich glycoprotein (HRG) in a sample obtained from a subject, such as a body fluid sample, tissue sample, or an ovum sample. The outcome of the IVF involving the subject in terms of the chances of the woman becoming pregnant is then predicted based on the determined isoform(s) of the HRG protein found in the body sample.

In another embodiment, DNA of the subject is extracted from the sample. Single nucleotide polymorphism genotyping is then performed on at least a portion of exon five of HRG. The outcome of IVF is predicted based on the result from the genotyping.

In more detail, if the subject is determined to be Ser/Ser homozygote for the SNP polymorphism in exon five of the HRG gene the outcome of the IVF in terms of successful pregnancy is predicted to be very low. Pro/Ser heterozygote subjects are predicted to have low chances of successful pregnancy of IVF whereas Pro/Pro homozygote subjects are predicted to have a comparatively increased or higher chance of successful pregnancy with IVF.

Other aspects relates to methods of predicting fertility status of a woman. The methods then involve determining the isoform of HRG in a body sample obtained from the woman or performing SNP genotyping on at least a portion of exon five of the HRG gene on DNA extracted from the body sample. The methods then predict the fertility status of the woman based on the determined HRG isoform(s) or based on the SNP genotyping.

Other aspects relates to increasing the success of pregnancy of a woman undergoing IVF. A method involves administering the proline isoform of HRG or an amino acid fragment thereof comprising the proline residue of amino acid position 204 of the full-length HRG protein to the fluid or culture medium comprising the ova to be or having been fertilized in vitro.

The proline isoform of HRG or an amino acid fragment thereof comprising the proline residue of amino acid position 204 of the full-length HRG protein are also employed herein as fertility promoting medicament and can be used in vaginal compositions.

Further aspects relate to a method of increasing success of pregnancy of a woman, such as a woman undergoing IVF. The method comprises administering the proline isoform of HRG or an amino acid fragment thereof comprising the proline residue of amino acid position 204 of the full-length HRG protein to the woman.

BRIEF DESCRIPTION OF THE DRAWINGS

The invention, together with further objects and advantages thereof, may best be understood by making reference to the following description taken together with the accompanying drawings, in which.

DETAILED DESCRIPTION

The present invention generally relates to fertility prediction and fertility promotion. An aspect of the invention relates to in vitro fertilization (IVF) and in particular to techniques for predicting successful implantation of an embryo during IVF and increasing the chances of successful pregnancy with IVF. Other aspects relate to predicting fertility status of a woman and techniques for increasing success of pregnancy.

Embodiments as disclosed herein are based on the discovery of a predictor that can be used for predicting fertility status and predicting success of IVF. This predictor is the Histidine-rich glycoprotein (HRG) and the gene that encodes HRG.

HRG is an abundant multi-domain plasma protein known to bind to a wide range of ligands including fibrinogen, heparin, and thrombospondin. It is involved in angiogenesis having both angiogenic and antiangiogenic properties. It is believed to be pro-angiogenic by blocking the antiangiogenic effects of trombospondin and/or, by binding to plasminogen or to plasmin, assisting in promoting cell migration and invasion. However, the antiangiogenic effect of HRG has been suggested to be mediated by signal transduction targeting focal adhesions and thereby interrupting Vascular Endothelial Growth Factor (VEGF)-induced endothelial cell motility. Another antiangiogenic property is thought to be mediated by preventing Fibroblast Growth Factor (FGF) from binding to the extracellular matrix and on endothelial cell surfaces. This thereby prevents angiogenic growth factors from being released from the extracellular matrix and also sends an antiangiogenic signal to endothelial cells. HRG is also involved in fibrinolysis and coagulation, complement activation, and immune complex clearance. HRG is produced in liver parenchymal cells and has been shown to be transported both as a free protein in serum and in the granules in platelets.

The HRG gene is localized to chromosome 3q27 in humans. The gene contains seven exons and six introoses. Exon five contains a single nucleotide polymorphism (SNP), denoted C/T rs9898 in the art, causing proline (Pro) and serine (Ser) polymorphism. Serine at this position introduces a consensus N-glycosylation site (Asn-X-Ser/Thr). The introduction of a N-glycosylation site causes the addition of an extra carbohydrate group to the asparagine (Asn) residue. As a result of the glycosylation, the molecular weight is slightly higher for the Ser isoform of HRG as compared to the Pro isoform. This means that the particular isoform of HRG from a subject can be determined by analyzing the molecular weight of HRG. For instance, when running a Western blot analysis it is possible to distinguish between the different HRG isoforms, which appear as a 75 kDa (Pro isoform) and a 77 kDa (Ser isoform) band, respectively.

The sequences (SEQ ID NO: 1 and SEQ ID NO: 2) below illustrate a portion of the nucleotide sequence of exon 5 of the HRG gene and the corresponding amino acid sequence. The C/T rs9898 polymorphism is evident from the sequences and results in either proline (with codon CCC) or serine (with codon TCC) at the relevant site.

```
. . . GTG CGG AAC TGC [C/T]CC AGA CAC CAT TTC . . .

. . . Val Arg Asn Cys Pro/Ser Arg His His Phe . . .
```

In the literature as represented by Hermann et al, The histidin-rich glycoprotein Pro186Ser polymorphism is not related to myocardial infarction in the ECTIM study, *Thromb Haemost*, 1998, 79(2):359-361, this polymorphism of HRG is generally denoted as Pro186Ser indicating that the relevant amino acid residue would be amino acid number 186 of the HRG protein. However, protein databases, such as UniProt and NCBI, instead refer to amino acid number 204 of HRG, i.e. Pro204Ser, as the relevant position for the polymorphism. The reason for this difference is that the HRG protein comprises a signal peptide that can be cleaved from the protein. HRG with the signal peptide has the amino acid number 204 as the relevant position for the polymorphism, whereas this polymorphism position in HRG without the signal peptide is amino acid number 186. However, in all these cases the relevant Pro/Ser amino acid and the CCC/TCC codon is present within the above presented context or locus of the HRG protein and HRG gene, respectively.

Studies have been conducted that verify that there is a significant connection between success of pregnancy and success of an in vitro fertilization of a human woman and the HRG isoform and the gene variant of HRG encoding either Pro or Ser at the above presented position of HRG.

In the following, the expression Ser isoform is used to denote the HRG isoform that has serine as amino acid at the position indicted in the portion of the amino acid sequence of HRG presented above, whereas Pro isoform denotes the HRG isoform that instead has proline as amino acid number at this position.

Figure 2:
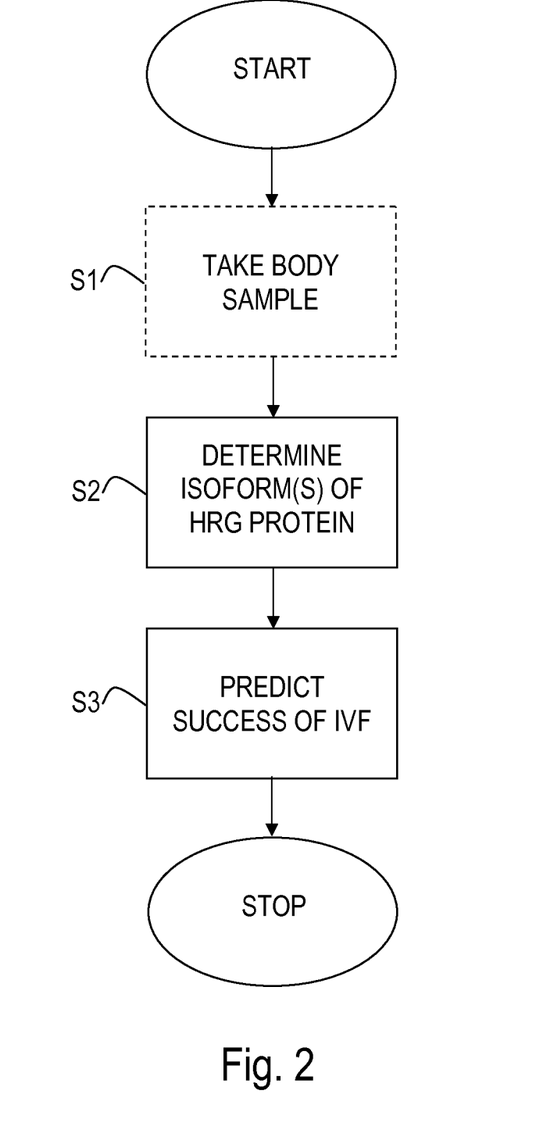
FIG. 2 is a flow diagram illustrating a method of predicting the outcome of in vitro fertilization according to an embodiment including analyzing HRG on protein level.

With reference to FIG. 2, an aspect therefore relates to a method of predicting success of an vitro fertilization of a woman or predicting the outcome of an in vitro fertilization of a woman in terms of successful pregnancy or not. The method optionally comprises taking a body sample comprising the HRG protein from at least one of the woman and the man in the couple undergoing IVF in step S1. Any body sample that comprises at least detectable amounts of HRG can be used according to this aspect. This means that both body tissue samples and body fluid samples can be used. Generally body fluid samples are preferred since they are typically easier to take and handle than body tissue samples. Non-limiting but preferred body fluid samples that can be used according to this aspect are follicular fluid samples, plasma samples and blood samples.

According to the aspect, the isoform or isoforms of HRG present in the body sample obtained from the woman and/or the man is determined in step S2. Alternatively, or in addition to determining the isoform of HRG from the body sample obtained from at least one of the woman undergoing IFV and the man donating sperm fertilizing at least one ovum in vitro to form at least one embryo to be implanted into the uterus of the woman, a sample obtained from an ovum of the at least one ovum can be investigated in terms of HRG isoform(s). Thus, instead of or as a supplement to taking a body sample from the woman, a sample obtained from one of the ova from the woman could be used or indeed a sample obtained from the resulting embryo. Determining the isoform of HRG from an ovum sample is in particular suitable if the ova comes from an ova donator and not the woman into which at least one fertilized ovum, i.e. an embryo, is to be implanted.

The estimated success of the in vitro fertilization of the woman or the outcome of the in vitro fertilization of the woman is then predicted in step S3 based on the determined isoform or isoforms of HRG in the body sample and/or ovum/embryo sample. Success of in vitro fertilization is regarded herein as an in vitro fertilization that leads up to pregnancy.

It is preferred if the sample is taken at least from the woman or the ovum but preferably both from the woman or ovum and the man. Alternatively, the sample can be taken only from the man of the couple involved in the IVF and donating the sperm that is used to fertilize the ova of the woman in vitro.

As is discussed in more detail herein, women being homozygote for the Ser isoform has very low and next to zero chance of successful pregnancy with in vitro fertilization. Women having both the Ser isoform and the Pro isoform have slightly better chances of successful in vitro fertilization leading up to fertilization and pregnancy, though they still had a low success rate. This should be compared to women that are homozygote for the Pro isoform that have significantly better chances of successful in vitro fertilization as compared to women with the Ser isoform. It is expected that the success of IVF in terms of the woman becoming pregnant is also dependent on the HRG isoforms of the man denoting sperm that are used for fertilizing the ova in vitro.

As is further disclosed herein, also the embryo produces HRG and it is believed that HRG from the embryo could be important for the chances of successful pregnancy. The chances of successful pregnancy is therefore dependent on the HRG isoform(s) of the embryo, which in turn are dependent on the genetic make-up of the ova-donating woman and the sperm-donating man.

In a preferred embodiment, the determination of the isoform in the (body) sample is performed by estimating the molecule weight of the HRG in the (body) sample. There is a detectable molecular weight difference between the two HRG isoforms due to the introduction of the N-glycosylation site with the Ser isoform. As a consequence, any molecular weight determining technique that can be applied to (body fluid) samples and that is capable of differentiating between the HRG isoforms, i.e. molecular weight of 75 kDa versus 77 kDa as determined from Western blot analysis, can be used according to the embodiments.

A simple, cost effective and fast such technique is Western blot that allows determination of the HRG isoforms in a (body) sample within a couple of hours. Western blot should, though, merely be seen as an illustrative example of molecular weight determining technique that can be used.

The two HRG isoforms do not necessarily have to be determined and identified based on molecular weight measurements. In an alternative approach, an ELISA test can be used to detect the presence of one or both HRG isoforms in a (body) sample. The ELISA test is then based on antibodies that bind specifically to the Ser isoform but not to the Pro isoform, antibodies that bind specifically to the Pro isoform but not the Ser isoform or preferably antibodies that bind specifically to the Ser isoform but not the Pro isoform and antibodies that bind specifically to the Pro isoform but not the Ser isoform. In the two former cases, only a single ELISA test need be used. Thus, if the ELISA test verifies the presence of the Ser isoform the predicted success of IVF is set to low, i.e. either homozygote or heterzygote for the Ser isoform. If the ELISA test cannot detect the presence of the Ser isoform using the antibodies, the woman is Pro/Pro homozygote and therefore has comparatively higher predicted success of IVF. If the antibodies instead bind specifically to the Pro isoform and the ELISA does not detect the presence of any HRG, the woman is determined to be Ser/Ser homozygote and therefore has very low predicted chance for success of IVF. Detection of the Pro isoform implies that the woman might have high chance of successful IVF (Pro/Pro homozygote) or low but not very low chance of successful IVF (Pro/Ser heterozygote). It is though preferred to run two different ELISA tests to verify whether the woman is Ser/Ser homozygote, Pro/Pro homozygote or Pro/Ser heterozygote.

Monoclonal antibodies against the two different HRG isoforms that are used in the ELISA tests can, for instance, be manufactured according to techniques well known in the art. Briefly, monoclonal antibodies are typically made by fusing myeloma cells with the spleen cells from a mouse that has been immunized with the desired antigen. However, recent advances have allowed the use of rabbit B-cells.

Other techniques known in the art for producing antibodies can alternatively be used.

Actually, any analysis that can be used in protein diagnostic in order to verify the presence of a particular HRG isoform can be used according to the invention.

When utilizing a molecular weight determining method for determining the HRG isoform in the (body) sample, the method preferably involves determining the presence of at least one of the 75 kDa and the 77 kDa isoforms of HRG. In the following the 75 kDa isoform denotes the HRG isoform that has a molecular weight of 75 kDa as determined by Western blot and corresponds to the Pro isoform. Correspondingly, the 77 kDa isoform denotes the HRG isoform having a molecular weight of 77 kDa as determined by Western blot and corresponding to the Ser isoform.

The prediction of IVF success is then performed based on the presence of the 75 kDa isoform, the presence of the 77 kDa isoform or based on the presence of both the 75 kDa and the 77 kDa isoforms. If it is determined that the (body) sample comprises the 77 kDa isoform of HRG, the prediction involves predicting a low success of IVF. Furthermore, if the (body) sample comprises both the 75 kDa and the 77 kDa isoforms, the success chances of IVF is determined to be low, whereas if the (body) sample comprises only the 77 kDa isoform, the chances are predicted to be very low. Subjects having respective (body) samples with only the 75 kDa isoform of HRG are predicted to have a comparatively high chance of IVF success.

The expressions low, very low and high as used herein with reference to success of IVF are merely given as relative terms that define how the success chances are for the three different categories of women, i.e. Ser/Ser homozygote, Pro/Ser heterozygote and Pro/Pro homozygote. Experimental results have been conducted in two different studies. In both these studies none of the Ser/Ser homozygote women became pregnant from the IVF, they are thereby regarded as having very low chance of IVF success. 17% and 33% of the Pro/Ser heterozygote women undergoing IVF became pregnant in the two studies, whereas 57% and 70% of the Pro/Pro homozygote women became pregnant.

Low chance of success thereby implies that the chances of getting pregnant from IVF is lower than average and high chance of success thereby implies that the chances of pregnancy is higher than the average of the human population.

The prediction of IVF success does not necessarily have to be conducted based on HRG isoform analysis on the protein level. In clear contrast SNP genotyping can be used to thereby instead conduct the analysis on DNA basis.

Figure 3:
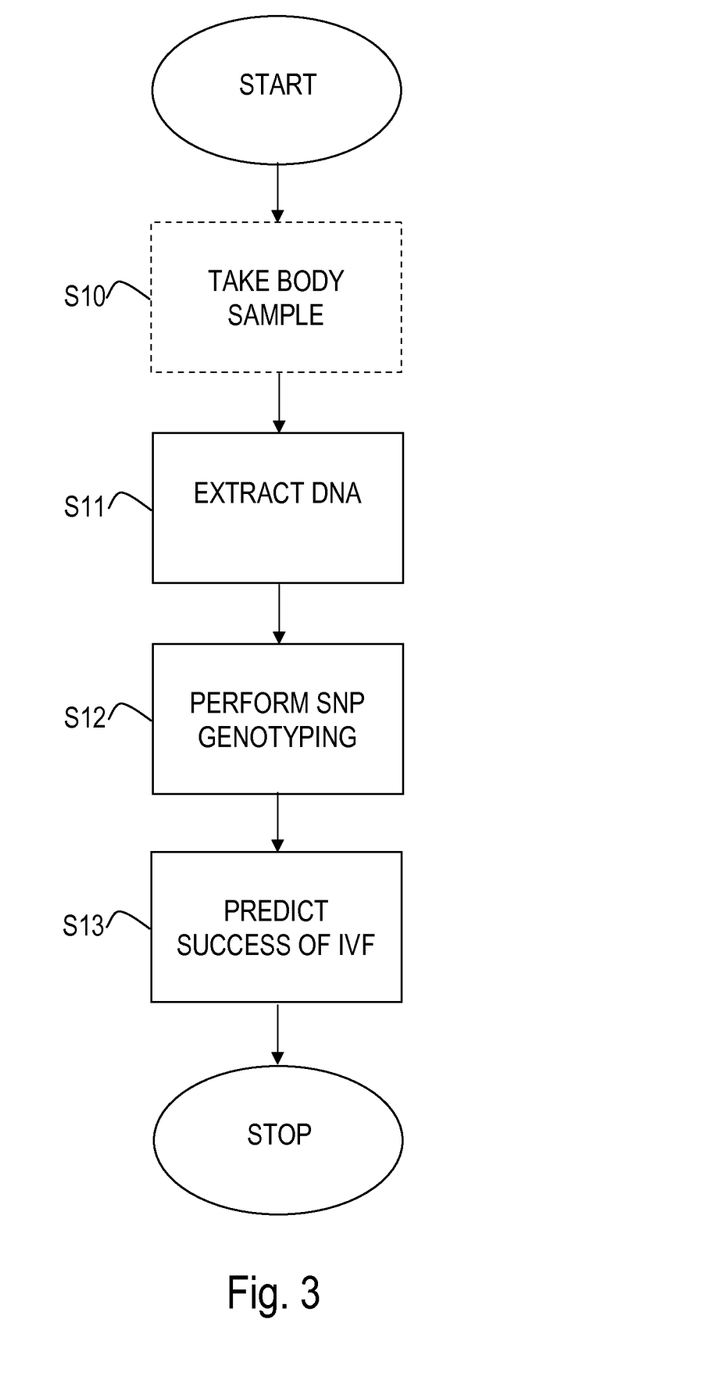
FIG. 3 is a flow diagram illustrating a method of predicting the outcome of in vitro fertilization according to another embodiment including analyzing HRG on genetic level.

With reference to FIG. 3, another aspect thereby relates to a method of predicting success of an IVF of a woman or predicting outcome of an IVF for a woman by optionally taking a body sample from a female and/or male subject undergoing IVF in step S11. The body sample can be a body tissue sample or a body fluid sample. Actually, any body sample from the subject comprising the DNA of the subject can be used in the method. The body sample is preferably a body fluid sample, such as a plasma or blood sample. Alternatively, or in addition, a sample obtained from one or more of the ova that are fertilized in vitro can be used.

DNA of the subject is extracted in step S11 from the (body) sample using techniques well known in the art. A non-limiting example of extracting DNA from a (body) sample is to use the DNA extracting kit provided by Qiagen.

SNP genotyping is then performed in step S12 on at least a portion of exon five of HRG using the DNA extracted in step S11. The SNP genotyping in particular verifies the particular nucleotide sequence of the HRG with regard to the C/T rs9898 polymorphism present in exon five of the HRG gene The success of IVF and the outcome of the IVF, i.e. chance of getting pregnant, for a woman undergoing IVF are predicted based on the SNP genotyping in step S13.

In similarity to the method discussed above in connection with FIG. 2 and conducted on the protein level, the nucleotide based analysis disclosed above can be made on the woman, the man or both the woman and the man of a coupled involved in IVF. In addition, or alternatively, the nucleotide based analysis can be made on the ova or the resulting embryo after fertilization.

As is well known in the art, SNP genotyping relates to techniques capable of determining a single base pair mutation at a specific locus. Various techniques can be used to perform the SNP genotyping in order to determine whether the subject is heterozygote or homozygote for proline or serine at the relevant position of HRG. Non-limiting techniques that can be used include the following ones.

Dynamic allele-specific hybridization (DASH) and molecular beacons used in SNP detection by means of a specifically engineered single-stranded oligonucleotide probe. If a molecular beacon is designed to match a wild-type allele ( . . . AACTGCCCCAGACAC . . . ) and another to match the mutant of the allele ( . . . AACTGCTCCAGA-CAC . . . ), the two can be used to identify the genotype of an individual. If only the fluorophore wavelength of the first probe is detected during the assay then the subject is homozygous to the wild type. If only the wavelength of the second probe is detected the subject is homozygote to the mutant allele. Finally, if both wavelengths are detected the subject is Ser/Pro heterozygote.

Further techniques that can be used include SNP microarrays in which probes are arrayed on a small chip.

Also enzyme-based methods can be used including restriction fragment length polymorphism (RFLP); PCR-based methods, such as Tetra-primer ARMS-PCT; flap endonuclease (FEN) based methods; primer estension; Taqman assay for SNP genotyping; oligonucleaotide ligase assays. Further techniques include single stranded conformation polymorphism; temperature gradient gel electrophoresis (TGGE); denaturing high performance liquid chromatography (DHPLC); high-resolution melting analysis and SNPlex sold by Applied Biosystems.

The SNP genotyping is performed in order to determine the HRG allele of the subject. This means that the SNP genotyping is conducted to verify whether the subject has the allele with nucleotide cytosine (C) to form the codon CCC encoding proline or the allele with nucleotide thymine (T) instead of C to form the codon TCC encoding serine instead of proline. As has been thoroughly discussed above, a woman that is homozygote for the T allele has a very low chance of successful IVF, a woman C/T heterozygote has a low chance of successful IVF and a woman C/C homozygote has a comparatively high chance of successful IVF.

It is also possible to conduct a sequencing of exon five of HRG or at least the portion of exon five comprising the relevant allele locus in the HRG gene. The determined nucleotide sequence is then used to conclude whether the subject is homozygote for the T allele, homozygote for the C allele or is heterozygote, i.e. comprises the T allele on the locus on one of chromosome 3 and the C allele on the locus of the other chromosome 3.

HRG is not only a marker or predictor of pregnancy outcome in IVF. Experimental data presented herein further supports that HRG can be used as a marker or predictor employed for predicting fertility status of a woman in general. The method then involves, in an aspect, determining the isoform of HRG in a body sample obtained from the woman. The body sample can be any of the previously discussed body samples. The fertility status of the woman is then predicted based on the determined HRG isoform. The HRG isoform can then be utilized to predict whether there is a risk of the woman having abnormal or impaired fertility status leading to increased chances of miscarriage. For instance, presence of only the 77 kDa isoform of HRG is more common in the group with habitual abortion, also referred to as recurrent miscarriage or recurrent pregnancy loss (RPL), in early pregnancy. The prediction of fertility status is then preferably performed based on the presence of the 75 kDa and/or 77 kDa isoforms of HRG in the body sample as described above. In particular, the woman is predicted to have abnormal or impaired fertility status, such as having increased risk of habitual abortion, based on the presence of the 77 kDa isoform of HRG in the body sample obtained from the woman, preferably based on the presence of the 77 kDa isoform of HRG but the absence of the 75 kDa isoform of HRG. Correspondingly, the woman is predicted to have normal fertility status based on the absence of the 77 kDa isoform of HRG but the presence of the 75 kDa isoform of HRG in the body sample.

The determination of the HRG isoform(s) according this aspect can be conducted in the same way as for predicting pregnancy outcome of women undergoing IVF as described in the foregoing.

The prediction of fertility status of a woman must not necessarily be conducted based on HRG isoforms but could instead be performed by extracting DNA of a body sample obtained from the woman. SNP genotypes, as discussed in the foregoing, is then performed of at least a portion of exon five of the HRG gene on the extracted DNA and the fertility status of the woman is predicted based on the SNP genotyping.

In an embodiment, the woman is predicted to have abnormal or impaired fertility status, such as having an increased risk of habitual abortion, if the nucleotide sequence of at least a portion of the exon five has the T allele of the C/T rs9898 polymorphism and in particular being homozygote for the T allele. Correspondingly, a woman is preferably predicted to have normal fertility status if the nucleotide sequence of at least a portion of the exon five has the C allele and preferably is homozygote for the C allele of the C/T rs9898 polymorphism.

Extracting DNA of the body sample and performing SNP genotyping can be performed as previously described herein.

The experimental data presented herein indicates that the presence of the Pro isoform of HRG seems to be vital or at least very important for successful pregnancy by means of IVF. An aspect therefore relates to a method of increasing the success of pregnancy of a woman undergoing IVF. The method then involves administering the Pro isoform of HRG or an amino acid fragment (peptide) thereof to the culture medium containing the ovum or ova that is or are fertilized in vitro to get one or more embryos. The amino acid fragment, which is further described herein, comprises the proline residue of amino acid number 204 in the full-length HRG protein. This means that the ova are thereby exposed to the Pro isoform of HRG or the Pro-containing amino acid fragment before, during or after in vitro fertilization through the addition of the Pro isoform to the culture medium. In a preferred embodiment, the Pro isoform of HRG or amino acid fragment is preferably added to the fluid or culture medium before and/or during in vitro fertilization of the ova. In a particular embodiment of this aspect, at least one of the woman, from which the ova comes, and the man donating the sperm is confirmed to be Pro/Ser heterozygote or Ser/Ser homozygote The Pro isoform of HRG or a peptide corresponding to a fragment of the HRG protein comprising the amino acid Pro of amino acid number 204 is, in an aspect of the embodiments used as fertility promoting substance. The peptide preferably comprises at least 10 amino acids, preferably at least 14 amino acids. An embodiment of preferred such peptide or Pro-containing amino acid fragment constituting a 14 amino acid fragment of HRG is Phe-Ser-Val-Arg-Asn-Cys-Pro-Arg-His-His-Phe-Pro-Arg-His (SEQ ID NO: 9). In this peptide sequence the relevant proline residue corresponding to proline at amino acid number 204 in HRG is marked in bold.

In further embodiments, the peptide preferably comprises at least 15 amino acids and more preferably at least 20 amino acids, such as at least 25 amino acids, at least 30 amino acids or more preferably at least 35 amino acids. The peptide preferably has the same amino acid sequence as a fragment of the HRG protein and comprises the amino acid Pro at position 204. The proline residue is preferably centered in the peptide. The peptide does not necessary have to have 100% homology with the corresponding portion of the HRG protein. The embodiments also encompass peptides having at least 80%, preferably at least 85% and more preferably at least 90% or at least 95% homology with the HRG protein. However, the peptide comprises the proline, preferably close to the center of the peptide sequence, even though one or a few other amino acids may differ from the amino acid sequence of the HRG protein.

A peptide having the amino acid sequence Arg-Gly-Gly-Glu-Gly-Thr-Gly-Tyr-Phe-Val-Asp-Phe-Ser-Val-Arg-Asn-Cys-Pro-Arg-His-His-Phe-Pro-Arg-His-Pro-Asn-Val-Phe-Gly-Phe-Cys (SEQ ID NO: 7) have been tested and can be used as fertility promoting agent according to the embodiments.

An aspect relates to a molecule comprising a peptide as defined above for use in manufacturing a fertility promoting medicament. The molecule preferably is the peptide as defined in SEQ ID NO: 9 or SEQ ID NO: 7 or comprises the amino acid sequence of SEQ ID NO: 9 or SEQ ID NO: 7. In a particular embodiment, the molecule is the proline isoform of HRG, either the proline isoform of HRG comprising the signal peptide as mentioned above of the proline isoform of HRG without the signal peptide.

A further related aspect is a method of increasing success of pregnancy or promoting fertility of a woman comprising administering a molecule as mentioned above to the woman. The method preferably comprises administering a molecule as defined in SEQ ID NO: 9 or SEQ ID NO: 7 or comprising the amino acid sequence of SEQ ID NO: 9 or SEQ ID NO: 7 to the woman. In a particular embodiment, the molecule is the proline isoform of HRG (either with or without the signal peptide).

The molecule can be administered to the woman prior, during and/or following implantation of an embryo into the uterus of the womon if the woman is undergoing IFV. In a particular embodiment, the molecule is preferably intended to be administered to the woman at least prior to implantation of the fertilized zygote into the uterus of the woman. The administration is preferably conducted by injecting the molecule, such as the Pro isoform of HRG, into the endometrium of the woman before implantation of the embryo. An alternative or additional administration site can be into the cavity of the uterus through the cervix. This aspect can also be combined with the administration of the molecule, such as Pro isoform of HRG, to the medium comprising the ova/embryo.

In a particular embodiment, the administration of the molecule, such as Pro isoform, as described above is in particular effective if at least one of the woman and a man donating sperm to fertilize at least one ovum of the woman in vitro is heterozygote or preferably homozygote for the serine isoform of HRG.

The molecule, i.e. peptide or Pro isoform of HRG, is preferably provided as a vaginal composition comprising the peptide or Pro isoform of HRG and at least one pharmaceutically acceptable carrier or excipient applicable for intravaginal administration.

Several types of formulations are generally available for intravaginal administration including vaginal tablets, hard and soft gelating capsules, creams, gels, suppositories, pessaries, foams, ointments, films, tampons, vaginal rings, douches and solutions. The formulation is advantageously in the form of a vaginal capsule, tablet or insert, a vaginal gel or cream or in the form of a vaginal solution.

Examples of suitable pharmaceutically acceptable carriers or excipients can be selected from excipients listed in Garg et al., Compendium of Pharmaceutical Excipients for Vaginal Formulations, *Pharmaceutical Technology Drug Delivery* 2001, pages 14-24.

It could also or alternatively be possible to screen the embryo for production of HRG. The particular isoform(s) produced by the embryo then defines whether the molecule, such as Pro isoform of HRG, should be administered to the fluid or culture medium comprising the embryo and/or administered to woman into which the embryo is to be implanted. Thus, if the embryo produces the Ser isoform of HRG either alone or together with the Pro isoform, administration of the molecule, such as Pro isoform of HRG, to the culture medium and/or to the woman should be initiated.

The Pro isoform of HRG employed in these aspects is preferably the Pro isoform of human HRG and more preferably the Pro isoform of recombinant human HRG.

The concentration of the molecule, such as Pro isoform of HRG, that is added to the medium or administered to the woman can be selected to be in the concentration range of natural HRG in the human female population. This concentration range can non-inventively be determined by the person skilled in the art using techniques well known in the art.

A further aspect also relates to the molecule, such as Pro isoform of HRG, for use in therapy, as a medicine or as a medicament. A particular aspect relates to the molecule, such as Pro isoform of HRG, for use in increasing success of pregnancy of a woman, in particular a woman undergoing in vitro fertilization and particularly where the woman and/or sperm-donating man is Pro/Ser heterozygote or Ser/Ser homozygote of HRG. A further particular aspect relates to the use of the molecule, such as Pro isoform of HRG, for the manufacture of a medicament for increasing success of pregnancy of such a woman.

EXPERIMENTS

In order to analyze the importance of HRG in fertility/infertility 24 women attending to the Centre of Reproduction, Akademiska sjukhuset, Uppsala were asked to be included in the study. Follicular fluid from the ovaries and plasma were collected and frozen. Western blot was performed and we found two isoforms of full-length HRG corresponding to the molecular weight 75 and 77 kDa. From the samples analyzed 4 women seemed to be homozygous carriers of Ser/Ser with only one band on the gel at molecular weight 77 kDa. 6 of the women were heterozygous carriers with two bands on the gel (Proline/Serine) and 14 women had only the smaller protein indicating that they were homozygous for Proline/Proline.

The study was approved by the Regional Ethics Committee of the Medical Faculty of Uppsala and informed consent was obtained from each patient included in the study. No reimbursement was given to patients participating. All study patients were included at the Department of Women's and Children's Health, Uppsala University Hospital, Uppsala, Sweden.

A well-regulated angiogenesis is crucial for proper embryo implantation, embryogenesis, and pregnancy development. Monitoring the presence and distribution of angiogenic regulators in the female reproductive tract and in the early embryo is important for a broader understanding of the molecular aspects of fertility, embryogenesis, and pregnancy. HRG is a glycoprotein involved in angiogenesis. Its presence in the female reproductive tract or in embryos has not previously been studied. Follicular fluid, culture medium, and embryos were obtained from patients undergoing IVF. Biopsies from inner genitalia and placenta were collected at surgery. HRG presence was investigated by immunohistochemistry and Western blot. PCR was used to determine HRG expression in tissues or by embryos. We identified HRG in follicular fluid, the female reproductive tract, and placenta, as well as in the embryo. Moreover, HRG expression was observed in blastocysts. Thus, the angiogenic properties of HGF seems to affect fertility.

Collection of Follicular Fluid, Culture Medium and Embryos

Follicular fluid, culture medium, and embryos were collected from couples undergoing controlled ovarian hyperstimulation for IVF. A plasma sample was taken the same day as oocyte retrieval. At oocyte retrieval, follicular fluid was collected in a 50 ml centrifuge tube (Falcon, N.J., USA) and pooled from each patient separately. Care was taken to avoid blood contamination. The samples were temporarily frozen at −20° C. and moved weekly to a −70° C. freezer.

Medium (CCM, Vitrolife, Kungsbacka, Sweden) that had been used for embryo culture was pooled in four samples. Three samples contained medium from embryos cultured until day 5, 6 or 7 respectively. These samples included medium where even embryos retarded in development had been grown. The fourth sample was medium pooled from exclusively blastocyst cultures. In each sample, medium was pooled from embryos originating from six to ten couples. The medium was frozen at −20° C. for one week.

Human preimplantation embryos, which were not of sufficient quality for embryo transfer or cryopreservation at day 2 or 3, were cultured in medium (G-1™ PLUS/G-2™ PLUS, Vitrolife AB, Kungsbacka, Sweden) according to routine protocols. They were harvested at different stages from the 2 cell stage to hatching blastocysts and used for immunohistochemistry.

Collection of Biopsies from Fallopian Tubes, Endometrium, Placenta, and Myometrium from Uterus At laparoscopic sterilization, Fallopian tubes and endometrial biopsies, collected by curettage, were gathered from healthy female volunteers. The Fallopian tubes used were in the follicle, post-ovulatory and luteal phase of the menstrual cycle. The endometrium samples were taken six days after ovulation. Uterine myometrial biopsies and placenta samples were collected immediately after Caesarean section performed on normal, healthy pregnancies. The tissue samples were rinsed in physiological saline solution (NaCl 9 mg/ml), fixed in 4% paraformaldehyde for up to 24 hours, and stored in 70% ethanol for a few weeks until embedded in paraffin wax according to routine procedures.

Western Blot of Follicular Fluid

The samples were separated using 4-12% gradient Bis-Tris NuPAGE (NP0321, Invitrogen, CA, USA) and for reducing conditions commercially available reducing agent (NP0004, LI-COR, Invitrogen, CA, USA) was added. Separated protein samples were transferred to Immobilon-FL membranes (IPFL00010, Millipore Corp, USA), optimized for low background fluorescence and incubated with blocking buffer (927-40000, Li-Cor Biosciences, UK). Western blot was performed with an anti-HRG antibody (HRG-0119, Lena Claesson-Welsh, Department of Medical Genetics and Pathology, Uppsala University, Uppsala, Sweden) directed towards the His/Pro-rich domain of HRG. Immunoreactive sites were detected by the fluorescently labeled anti-rabbit IRDye800 antibody (611-732-127/Rockland, USA) using the Odyssey infrared imaging system (Westburg).

Figure 1:
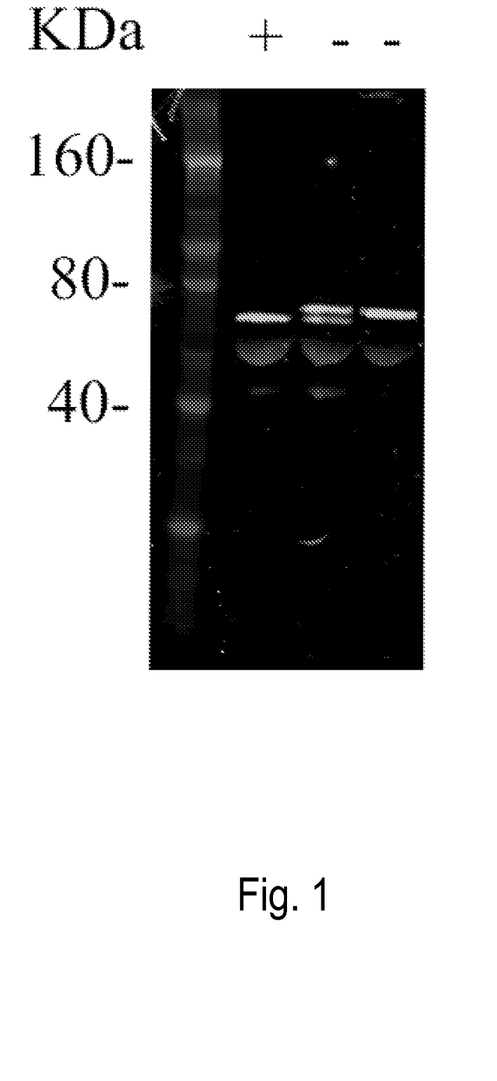
FIG. 1 illustrates a Western blot on follicular fluid from three different women illustrating how the different isoforms of HRG migrates in a gel. The upper/larger band corresponds to the isoform with Proline/Proline in the position of interest. The lower/smaller band indicates the isoform corresponding to the protein with Serine/Serine in the position of interest. The sample loaded in the middle is from a heterozygous woman with Serine/Proline in the same position. The woman with Proline/Proline became pregnant after in vitro fertilization, while the others did not.

Two isoforms of the full length HRG was detected in the Western blot analysis, corresponding to bands with a molecular weight of 75 and 77 kDa, see FIG. 1. Of the follicular fluid samples from the 24 women four had a single 77 kDa band (Ser/Ser homozygote), six had a double band (Pro/Ser heterozygote) and 14 had a single 75 kDa band (Pro/Pro homozygote). The total Ser allele frequency of this population is therefore 0.29.

Of the 24 women undergoing IVF, nine became pregnant. The Ser allele frequency was significantly lower among these pregnant women. Only one woman was Pro/Ser heterzygote and the other eight pregnant woman were Pro/Pro homozygote. This implies a Ser allele frequency of only 0.06. In addition, the pregnancy of the single Pro/Ser heterozygote woman had to be stopped since the fetus had lethal malformations.

Four of the 15 women that did not become pregnant with the IVF treatment were Ser/Ser homozygote, six were Pro/Ser heterozygote and only five were Pro/Pro homozygote. This gives a Ser allele frequency of 0.43. The difference between the group that became pregnant and the group that did not became pregnant is significant. Also the difference between the group of Ser/Ser homozygote and Pro/Ser heterozygote and the group of Pro/Pro homozygote is significant.

Table 1 below is an overview of the Western blot data on the genetic variation in HRG from follicular fluid from 24 women undergoing IVF.

TABLE 1

|  | Pregnant | Not pregnant | Total |
|---|---|---|---|
| Ser/Ser | 0 | 4 | 4 |
| Pro/Ser | 1 | 5 | 6 |
| Pro/Pro | 8 | 6 | 14 |
| Total | 9 | 15 | 24 |
| Ser allele frequency | 0.06 | 0.43 | 0.29 |

ELISA on Culture Medium and Plasma

The wells of a PVC microtiter plate were coated with a polyclonal HRG capture antibody (H00003273-B01P, AbNova, USA) in a bicarbonate buffer, pH 9.6, for 1 h at 37° C. followed by two washing steps using Tris-buffered saline (TBS). Blocking buffer containing 5% BSA was added for 1 h at 37° C. followed by two more washing steps using TBS. The samples were incubated for 45 min at 37° C. and then washed four times. For detection, a second antibody (HRG-0119, Lena Claesson-Welsh, Department of Medical Genetics and Pathology, Uppsala University, Uppsala, Sweden), was added for 1 h at 37° C., then followed by four steps of washing. Incubation with a biotinylated anti-rabbit IgG antibody (BA-1000, Vector Laboratories) was performed, washed, and then Streptavidin-conjugated HRP in TBS/0.1% Tween was added. Levels of HRG were analyzed at the optical density of 450 nm after adding a TMB (3,3',5,5'-tetramethylbenzidine) containing substrate and stopping solution (2M $H_2SO_4$). A standard curve of purified HRG was included in each trial.

ELISA was performed on culture medium to analyze if HRG is secreted by human embryos. This culture medium had been used to grow blastocysts. HRG was detected in each sample, see Table 2. Medium that had not been used for embryo culture was used as a negative control and did not contain a detectable level of HRG.

TABLE 2

|  | Day 5* | Day 6* | Day 7* | Blastocyst** |
|---|---|---|---|---|
| HRG (μg/ml) | 8.6 | 5.2 | 5.2 | 3.8 |

*All embryos were cultured to respective day including those retarded in development
**Only blastocysts were cultured Immunohistochemical Staining of Embryos Embryos were rapidly transferred from culture medium, briefly washed in Phosphate-buffered saline (PBS) containing 3 mg/ml polyvinylpyrrolidone (PVP), and then fixed with 2.5% paraformaldehyde in PBS for 15 minutes at room temperature. Following fixation, the embryos were permeabilized in PBS/PVP buffer containing 0.25% Triton X 100 for 30 minutes. Thereafter, the embryos were placed in PBS blocking buffer containing 0.1% bovine serum albumin (BSA) and 0.01% Tween 20 for 15 minutes. The primary antibody (HRG-0119, Lena Claesson-Welsh, Department of Medical Genetics and Pathology, Uppsala University, Uppsala, Sweden) was added in blocking buffer. The embryos were incubated overnight at 4° C. and then washed three times for 15 minutes each in blocking buffer to remove any unbound primary antibodies. The secondary antibody, Alexa 568 conjugated goat anti-rabbit (A11079, Invitrogen Corporation, Stockholm, Sweden), was diluted in blocking buffer and applied to the embryos for 60 minutes at room temperature in the dark. For negative controls, the primary or the secondary antibody was omitted in blocking buffer. After incubation, the embryos were briefly washed through a series of 25, 50, 75 and 100% citifluor (with DAPI) and then mounted on slides in antifade medium under a cover slip. Stained embryos were viewed in a confocal microscope (Zeiss, Germany) equipped with fluorescence optics and appropriate filters.

Figure 4:
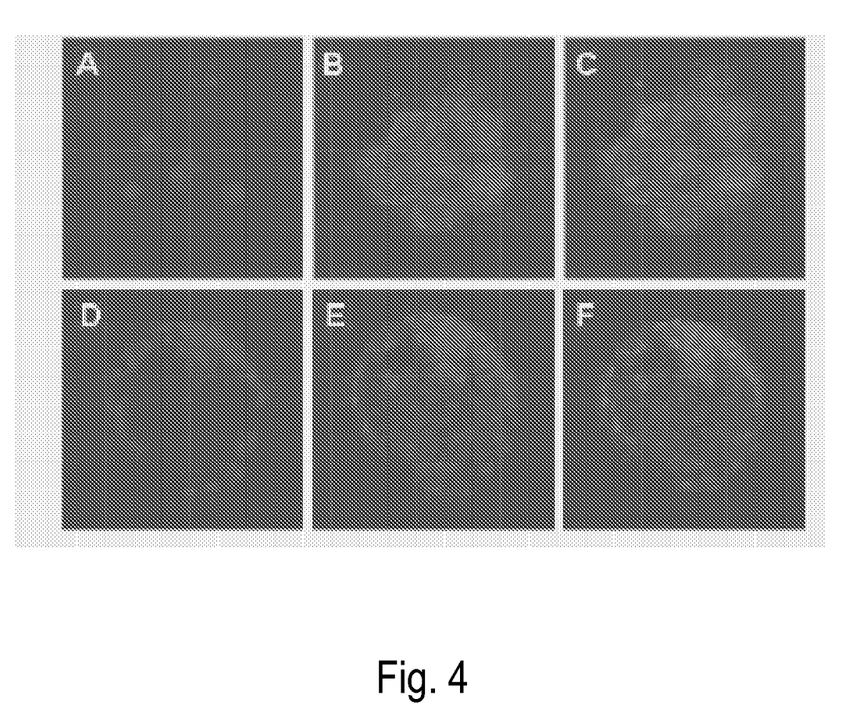
FIG. 4 illustrates immunohistochemistry of embryos. (A-C) 6-cell embryo (D-F) blastocyst. Using immunohistochemistry, Dapi (blue) indicates the location of all nuclei and HRG location is red. The combined picture overlaps DAPI and HRG; thus, both nuclei with and without HRG are observed in the blastocyst. In the blastocyst, HRG is seen in all cell cytoplasm and in some cell nuclei. HRG is not seen in the nuclei of the 6-cell embryo.

Immunohistochemical staining was performed to study the presence, localization, and intensity of HRG in preimplantatory embryos, see FIG. 4. HRG was present in all stages of development; from 4-cell stage through hatched blastocyst stage. It was detected in the cytoplasm of all cells in all preimplantatory embryos regardless of developmental stage. However, staining for HRG was identified only in a few nuclei of early cleavage stage embryos (25% of 4-8 cell stage embryos) but in later stages, HRG was more common in the nuclei (94% of blastocysts). No embryo exhibited HRG in all cell nuclei, see Table 3 below. Upon examination, it was discovered that HRG is autofluroscering but its endogenous signal was stronger than the background fluorescence meaning that there was a clearly distinguishable difference.

TABLE 3

|  | Total embryos | Embryos with HRG in some nuclei[a] | Embryous with HRG in some nuclei in inner cell mass[a] | Embryos with HRG in some culei in trophoblast[a] | Embryous with HRG in all cell cytoplasm |
|---|---|---|---|---|---|
| 4-5 cell stage embryo | 8 | 2/8[b] | — | — | 8/8 |
| 6-8 cell stage embryo | 8 | 2/8[b] | — | — | 8/8 |
| Total 4-8 cell stage embryo | 16 | 4/16 | — | — | 16/16 |
| Blastocyst | 12 | 11/12 | 9/12 | 11/12 | 12/12 |
| Expanded or hatched blastocyst | 6 | 6/6 | 6/6 | 6/6 | 6/6 |
| Total blastocyst | 18 | 17/18 | 15/18 | 17/18 | 18/18 |

[a]No embryo exhibited HRG in all nuclei
[b]Two of the eight embryos were embryos that had been cultured for 6 or more days but had retarded development. Neither exhibited HRG in its nuclei.
[c]Three embryos had been cultured for 6 or more days but had retarded development. Two of these three were the only ones in this group to exhibit HRG in their nuclei.

PCR on Embryo

PCR on eight blastocysts was performed using Taqman PreAmp Cells to CT Kit (Ambion INC, Austin, Tex., USA) with the following modifications: The pre-amplification and amplification steps were performed using the same amplification sequence as for the tissue (see below). SYBR green was used in the amplification step. Fluorescence data was acquired by measurements taken at every extension step and presented as a plot of fluorescence intensity versus cycle number. The cycle threshold value (Ct) was used to determine the presence of HRG.

To study if HRG was produced by the embryos, real time PCR analysis was performed. The mean CT value for HRG was 35.85±1.89 and for GAPDH 26.26±0.76, which is close to the detection limit for HRG mRNA.

Immunohistochemical Staining of Tissue

A section (5 μm) of paraformaldehyde-fixed, paraffin-embedded tissue (Fallopian tube, endometrium, placenta or myometrium) was deparaffinized in xylene, rehydrated through graded ethanol (99.5% 1×3 minutes, 95% 2×3 minutes, 70% 2×3 minutes) and washed in deionized water followed by TBS, pH 7.4. These slides were incubated in a citrate-buffer and heated in a microwave oven for 10 minutes at 650 W. Non-specific binding was blocked by incubation with 5% BSA in TBS for 1 hour. Sections were then incubated overnight at 4° C. in a humidified chamber with the affinity-purified rabbit anti-HRG antibody (HRG-0119, Lena Claesson-Welsh, Department of Medical Genetics and Pathology, Uppsala University, Uppsala, Sweden). The sections were washed in 0.01% Tween-20/TBS buffer. A biotinylated anti-rabbit antibody (Zymed Laboratories, Inc., CA, USA) was added for 1 hour at room temperature. Sections were washed and streptavidin conjugate horseradish peroxidase complex (Vector Laboratories, CA, USA) was added. After rinsing, the sections were exposed to chromogen solution using liquid DAB substrate kit (DAKO, Sweden) and counterstained with Mayer's hematoxylin. The appearance of a brown reaction product was observed by light microscopy. Negative control staining was performed by omitting either the primary antibody or the secondary antibody. Non-specific staining was not detected.

Figure 5:
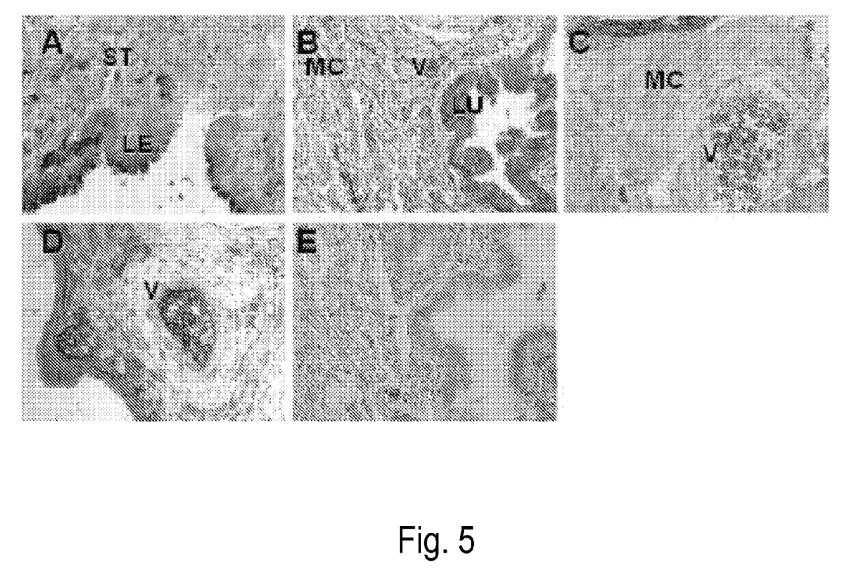
FIG. 5 illustrates immunohistochemical staining, in which HRG was detected in (A) endometrium, (B) Fallopian tube, (C) myometrium, (D) placenta, though not in (E) negative control. Abbreviations are as follow: ST=stroma cells, LE=luminal epithelium, MC=muscle cell, LU=lumen, V=blood vessel. The appearance of a brown reaction indicates positive staining.

The presence of HRG in the female reproductive tract was determined by immunohistochemical staining. HRG was detected in most cell types in the biopsies from human endometrium, see FIG. 5A, and Fallopian tube, see FIG. 5B. HRG was furthermore found in uterine myometrial cells, see FIG. 5C, and in endothelium, stroma, and trophoblasts in placental tissue, see FIG. 5D.

Preparation of RNA and Synthesis of cDNA

Samples from biopsies of endometrium, Fallopian tube, myometrium, and placenta were used for real-time PCR analysis. The frozen samples for real-time (RT) PCR were homogenized in a lysis buffer. RNA was extracted using RNeasy Mini-kit (Qiagen, Venlo, Netherlands). The concentration and purity of the RNA were measured using an Aguillent bioanalyzer 2100 (Agillent, Santa Clara, Calif., USA). A RIN value of <7 was obtained for all samples included in this study. Synthesis of cDNA from endometrial tissue samples was performed by using Superscript III First Strand Synthesis for RT-PCR (Invitrogen, Carlsbad, Calif., USA). Two micrograms of total RNA from tissue samples per reaction were reverse-transcribed using random hexamers as primers. Reverse-transcription was performed according to the manufacturer's instructions.

Real-Time PCR

RT-PCR reactions were performed using a Step-One Real-Time PCR System (Applied Biosystems, Foster City, Calif., USA). SYBR Green was used to detect the amplification. The reaction mixture consisted of 1×SYBR Green PCR master mix, 4 µL of the RT reaction mixture, corresponding to 4 ng cDNA, and the primer concentrations were 250 nM. The final reaction volume was 15 µL. cDNA was heated to 50° C. for 2 minutes and denaturized at 95° C. for 10 minutes. This was followed by 45 cycles of denaturation at 95° C. for 15 seconds and combined primer annealing/extension at 65° C. for one minute. Fluorescence data was acquired by measurements taken at every extension step and presented as a plot of fluorescence intensity versus cycle number. Each sample was run in duplicate and the target genes were normalized to glyceryl-aldehyde-3-phosphate dehydrogenase (GAPDH) as endogenous control. The forward and reverse primers for HRG were 5'-GCA GGG CGG GTC ACA AGG TCC ATA GTC (SEQ ID NO: 3) and 3'-CAC AAG TTC TGT CTC TTC AG (SEQ ID NO: 4) respectively and for GAPDH were 5'-GAA GGT GGT CGG AGT CAA C (SEQ ID NO: 5) and 3'-CAG AGT TAA AAG CAG CCC TGG T (SEQ ID NO: 6). The amplified product size for HRG was 916 bp, and for GAPDH 80 bp.

PCR was performed to determine whether HRG is expressed in female reproductive tract and placenta or not. No expression of HRG in tissue from Fallopian tube, endometrium, placenta, or myometrium was detected. Liver mRNA was used successfully as a positive control.

We have shown by immunohistochemistry that HRG is present in preimplantatory embryos and is detected more often in the nuclei as the embryo develops. Moreover, our ELISA and PCR data indicates that the embryo produces and secretes HRG. We have also found that HRG is present in medium where embryos have been grown, in follicular fluid, throughout the female reproductive tract, and in the placenta.

The HRG found in follicular fluid may reflect the angiogenic process in the development of the follicle and the oocyte. The heparin-binding angiogenic factors FGF and VEGF are known to be produced by the preovulatory follicle. It has been hypothesized that they are key regulators of the angiogenic balance in the follicle. HRG interacts directly and indirectly with angiogenic, antiangiogenic factors, and heparin and can possibly be important in follicle development. High VEGF levels in follicular fluid are associated with poor oocyte quality. If HRG binds to VEGF or other angiogenic factors, its presence in follicular fluid may also be of importance in the development of the oocyte.

Besides finding HRG in follicular fluid, we show by using immunohistochemistry that HRG is found in the embryo. HRG was detected in all cytoplasm in all embryos regardless of developmental stage. However, HRG was more commonly found in the nuclei of blastocysts than in embryos between the 4-8 cell stages, which is the time the embryos's genes are activated. Moreover, HRG was never found in all the nuclei of the same embryo, which suggests that HRG might be only by certain cells. HRG has probably different functions in early cleavage stage embryos compared with blastocysts. As there was no detectable level of HRG in the medium, which had not been used to culture embryos, it can be suggested that the protein seen in the nuclei using immunohistochemistry was produced by the embryo.

This is the first study showing that embryos produce HRG. Thus, since we show HRG is located in the nucleus of some cells in the blastocyst, in culture medium changed daily where blastocysts had been grown, and that it is in mRNA in the blastocyst, we conclude that, despite the low CT value for the embryo, the embryo produces HRG. It has been suggested that angiogenic factors secreted by the embryo signal to the endometrium to prepare for implantation. Further studies are required to determine if the expression of HRG by embryos is involved in this intricate communication between the embryo and the endometrium. VEGF and angiopoietins are associated with the development of a well-functioning placenta. It may also be possible that what we are observing is related to the beginning of this process. This is also supported by our earlier results showing that HRG is involved in the pathophysiology of early-onset preeclampsia as a consequence of inadequate levels of HRG in the placenta, see Kårehed et al., Fibrinogen and histidine-rich glycoprotein in early-onset preeclampsia, *Acta Obstet Gynecol Scand*, 89(1):131-139.

We have shown that HRG is present in female reproductive tract structures such as the Fallopian tube, endometrium, myometrium, and is also present in the placenta. As HRG exists in plasma, it may penetrate the reproductive tract and thus its presence in these tissues could simply be coincidental. However, as other angiogenic factors are known to exist within the reproductive tract and play an important role in fertilization and implantation, one might expect HRG to have a similar role. A number of different angiogenic factors existing in Fallopian tube secrete are of importance in assisting fertilization of the oocyte. Since HRG is known to be essential in the regulation of angiogenesis, HRG's presence in the Fallopian tube and endometrium may be needed for maturation and transportation of the embryo, as well as for preparation of the endometrium for implantation.

In order to verify the results from the Western blot study, SNP genotyping of Ser/Pro polymorphism (rs9898) in the HRG gene was conducted on plasma samples from 37 further women undergoing IVF.

TaqMan® SNP Genotyping Assay

Genomic DNA was prepared from blood samples taken from 37 women undergoing IVF treatment at Huddinge Hospital Sweden. The women were genotyped for the C/T rs9898 SNP in HRG exon 5, using the TaqMan® SNP Genotyping Assay. Briefly, PCR reactions were performed in a 96 well plate in a total volume of 25 µl for each reaction. Each reaction consisted of 1× TaqMan Universal PCR Master Mix (PCR buffer, ROX passive reference dye, dNTPs and AmpliTaq Gold polymerase), 1×SNP Genotyping Assay (sequence-specific forward and reverse primers to amplify the polymorphic sequence of interest i.e. HRG exon 5, TagMan® MGB probes labeled with VIC® dye to detect allele 1 sequence and with FAM™ to detect allele 2 sequence) and 10 ng of genomic DNA. Cycling conditions were initiated for 10 min at 95° C. followed by 40 cycles of 15 s at 2° C. and 1 min at 60° C. Real time fluorescence detection was performed. The Sequence Detection System (SDS) Software (Applied biosystems) was used to plot fluorescence (Rn)values based on the signals from each well. The plotted fluorescence signals indicated which alleles were present in each sample.

19 of the women became pregnant after 1 or 2 IVF treatments, whereas 18 of the 37 did not become pregnant. Five of the 19 pregnant women were Pro/Ser heterozygote and 14 were Pro/Pro homozygote. In consistency with the results from the Western blot study, none of the Ser/Ser homozygote women became pregnant. Two of the 18 non-pregnant women were Ser/Ser homozygote, ten were Pro/Ser heterozygote and six were Pro/Pro homozygote. The difference between the groups with regard to carrier of Ser instead of Pro in the HRG protein is statistically significant.

Table 4 below summaries the results from the SNP analysis of HRG rs9898 from DNA sample from 37 women undergoing IVF.

TABLE 4

|  | Pregnant | Not pregnant | Total |
|---|---|---|---|
| Ser/Ser | 0 | 2 | 2 |
| Pro/Ser | 5 | 10 | 15 |
| Pro/Pro | 14 | 6 | 20 |
| Total | 19 | 18 | 37 |
| Ser allele frequency | 0.13 | 0.39 | 0.26 |

Migration and Proliferation

By using a proliferation and a migration (chemotaxis) assay the importance of HRG as well as HRG peptides was analyzed. The peptides used correspond to a fragment of full-length HRG containing 35 amino acids covering position 204 in the protein; the proline of native HRG in that specific position is changed to serine. The amino acid sequences are: RGGEGTGYFVDFSVRNCPRHHFPRHPNVFGFCRAD (SEQ ID NO: 7, named HRGPro herein) and RGGEGTGYFVDFSVRNCSRHHFPRHPNVFGFCRAD (SEQ ID NO: 8, named HRGSer herein); the peptides were produced and purchased from Innovagen, Lund, Sweden.

Chemotaxis Assay

The assay was performed in a modified Boyden chamber using micropore nitrocellulose filters (8 µm thick, 8 µm pore) coated with type-1 collagen solution at 100 µg/ml (Vitrogen 100, Collagen Corp.). Cells (G10 and HEEC cells) were trypsinized and resuspended at a concentration of $5.5\times10^5$ cells/ml in serum-free culture medium containing 0.25% fetal calf serum (FCS). The cell suspension was placed in the upper chamber, and the serum-free medium containing 0.25% FCS and FGF-2 or VEGF, HRG or the HRGPro or HRGSer peptide, was placed below the filter in the lower chamber. As a positive control, medium containing 10% FCS was added to the lower chamber. After 4-6 h at 37° C., the medium was removed and the cells sticking to the filter were fixed in pure methanol and stained with Giemsa stain. The cells that had migrated through the filter were counted.

The effects of HRG, HRGPro and HRGSer on migration of G10 and HEE cells were examined by using a Boyden chamber. FGF (20 ng/ml) induced migration of G10 and VEGF (10 ng/ml) induced migration of HEE cells. A tendency that HRG (100 ng/ml) and HRGPro (100 ng/ml) inhibited VEGF-induced migration of G10 and HEE cells were detected. HRGSer (100 ng/ml) inhibited significantly ($p<0.05$) VEGF-induced endothelial cell migration.

Cell Proliferation Assay

Cells (G10 and HEEC) in culture medium supplemented with 10% FCS were seeded into 24-well dishes. After 2 h the medium was changed to starvation medium (culture medium containing 0.25% FCS) and the incubation continued for an additional 24 h. The medium was changed again at day 2 and day 4 (starvation medium), and at the same time FGF-2 or VEGF, HRG or HRG Pro or Ser containing peptide were added. As a control, cells were cultured in basal culture medium supplemented with 10% FCS. Cell numbers were scored after 5 days.

G10 cells (Porcine aortic endothelial cells) were cultured in starvation medium containing culture medium (Ham's F12) supplemented with 0.25% FCS. HRG (100 ng/ml) inhibited significantly proliferation of G10 cells (decrease of 24%) compared with culture in starvation medium. The proline containing peptide HRGPro (100 ng/ml) and the serine containing peptide HRGSer (100 ng/ml) did both inhibit proliferation with a decrease of 29% and 35% respectively. The effects of treatment with HRG, HRGPro and HRGSer were all significant, $p<0.05$ compared to culture in starvation medium. The effect of HRG compared with HRGPro was not significant, but the effect of HRGSer compared with treatment of HRG or HRGPro was significant, $p<0.05$.

Human endometrial endothelial (HEE) cells were cultured in starvation medium containing culture medium (3H) supplemented with 0.25% FCS. The number of HEE cells increased 6% when HRG (100 ng/ml) was added, with HRGPro (100 ng/ml) the number increased 13% and with treatment of HRGSer (100 ng/ml) the number of cells increased 86% compared with culture in starvation medium. The effect of HRG, HRGPro and HRGSer was significant ($p<0.05$) compared to culture in starvation medium, although there was no significance between with treatment of HRG or HRGPro.

We conclude that HRG, HRGPro and HRGSer affect endothelial cell proliferation and migration. The effect of HRGPro seems to follow the same pattern as full-length native HRG, whereas the effect of HRGSer differs. There is a difference between species (human and pig) and it is furthermore of importance from which kind of tissue the endothelial cells have been prepared; the effect on proliferation of endometrial endothelial cells seem to be unique compared with other sources of endothelial cells. Endometrial receptivity and endothelial cell function is of importance for successful implantation of an embryo and our results indicate that endometrial endothelial cells are sensitive to HRG and derivates or fragments thereof, which furthermore have implications on fertility. Endothelial cell migration and proliferation are part of the underlying mechanisms which need to cooperate before, during and after implantation of an embryo where physiological pathways such as regulation of angiogenesis, coagulation, immunity and need to function adequately.

Thus, the peptide HRGPro basically had the same effect towards migration and proliferation as the full-length protein HRG. However, the peptide HRGSer having a serine at amino acid position 204 instead of proline had significantly different effects.

It is therefore concluded that an amino acid fragment of HRG comprising the proline residue of amino acid position number 204 can be used to achieve similar therapeutic effects as the full length protein HRG.

Habitual Abortion

A case-control study of recurrent miscarriages was performed. A total of 730 women were included after a brief health examination. Number of pregnancies, miscarriages and children were registered as well as smoking habit, present health problems and medication. Venous blood samples were collected and buffy coat was prepared. DNA was extracted using QIAamp® DNA Blood Maxi kits (Qiagen, Venlo, the Netherlands) and the samples were then genotyped for the C/T rs9898 SNP in HRG, using the TaqMan® SNP Genotyping Assay (Applied Biosystems, Foster City, Calif., USA).

The SNP analysis showed that the Ser/Ser containing genotype was detected in 14% of the women, the Ser/Pro genotype in 44% and the Pro/Pro genotype in 42% of the total cohort of women with recurrent miscarriages. In women with recurrent miscarriages before gestational week 12 the Ser/Ser containing genotype was found in 22%, and in women with recurrent miscarriages after gestational week 12 in 11%.

The Ser/Ser genotype is therefore of importance in regulation of implantation/placentation since women carrying the Ser/Ser genotype are significantly more common in the group with recurrent miscarriages in early pregnancy compared to women with miscarriages in later pregnancy.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method of increasing success of pregnancy of a woman undergoing in vitro fertilization comprising administering a molecule comprising the amino acid sequence of SEQ ID NO: 9 to a fluid or culture medium comprising at least one ovum from said woman before, during or after fertilization of said at least one ovum in vitro by sperm from a man to form at least one embryo to be implanted into the uterus of said woman.

2. The method according to claim 1, wherein administering said molecule comprises administering a molecule comprising the amino acid sequence of SEQ ID NO: 7, the proline isoform of histidine rich glycoprotein, HRG, to said fluid or said culture medium.

3. The method according to claim 1, wherein administering said molecule comprises administering a peptide having the amino acid sequence of SEQ ID NO: 9 to said fluid or said culture medium.

4. A fertility promoting molecule consisting of the amino acid sequence of SEQ ID NO: 7.

5. A vaginal composition comprising a fertility promoting molecule according to claim 4 and at least one pharmaceutically acceptable carrier.

6. The method according to claim 2, wherein administering said molecule comprises administering a peptide having the amino acid sequence of SEQ ID NO: 7 to said fluid or said culture medium.

7. A fertility promoting molecule consisting of the amino acid sequence of SEQ ID NO: 9.

8. A vaginal composition comprising a fertility promoting molecule according to claim 7 and at least one pharmaceutically acceptable carrier.

* * * * *

UNITED STATES PATENT AND TRADEMARK OFFICE
CERTIFICATE OF CORRECTION

PATENT NO. : 8,637,471 B2
APPLICATION NO. : 13/638878
DATED : January 28, 2014
INVENTOR(S) : Karehed et al.

It is certified that error appears in the above-identified patent and that said Letters Patent is hereby corrected as shown below:

On Title Page:

Item 22, PCT Filed: Please correct "Mar. 31, 2011"
　　　　　　　　　　　to read -- Mar. 30, 2011 --

Item 57, Abstract, Line 6: Please correct "used to increases the success"
　　　　　　　　　　　to read -- used to increase the success --

In the Specification:

Column 1, Line 11: Please correct "by reference herein it their entireties."
　　　　　　　　　　　to read -- by reference herein in their entireties. --

Column 7, Line 28: Please correct "of the HRG gene"
　　　　　　　　　　　to read -- of the HRG gene. --

Column 9, Line 27: Please correct "or Ser/Ser homozygote"
　　　　　　　　　　　to read -- or Ser/Ser homozygote. --

Column 9, Lines 35-36: Please correct "of HRG is Phe-Ser-Val-Arg-Asn-Cys-Pro-Arg-His-His-Phe-Pro-Arg-His (SEQ ID NO: 9)."

to read -- of HRG is Phe-Ser-Val-Arg-Asn-Cys-Pro-Arg-His-His-Phe-Pro-Arg-His (SEQ ID NO: 9). --

Column 9, Lines 55-58: Please correct "sequence Arg-Gly-Gly-Glu-Gly-Thr-Gly-Tyr-Phe-Val-Asp-Phe-Ser-Val-Arg-Asn-Cys-Pro-Arg-His-His-Phe-Pro-Arg-His-Pro-Asn-Val-Phe-Gly-Phe-Cys (SEQ ID NO: 7)"

Signed and Sealed this
Twenty-ninth Day of April, 2014

Michelle K. Lee
*Deputy Director of the United States Patent and Trademark Office*

CERTIFICATE OF CORRECTION (continued)
U.S. Pat. No. 8,637,471 B2 to read -- sequence Arg-Gly-Gly-Glu-Gly-Thr-Gly-Tyr-Phe-Val-Asp-Phe-Ser-Val-Arg-Asn-Cys-Pro-Arg-His-His-Phe-Pro-Arg-His-Pro-Asn-Val-Phe-Gly-Phe-Cys (SEQ ID NO: 7) --